US011023679B2

(12) United States Patent
Allen et al.

(10) Patent No.: US 11,023,679 B2
(45) Date of Patent: Jun. 1, 2021

(54) APPARATUS AND METHOD FOR AUTOMATICALLY MAPPING VERBATIM NARRATIVES TO TERMS IN A TERMINOLOGY DICTIONARY

(71) Applicant: Medidata Solutions, Inc., New York, NY (US)

(72) Inventors: Patricia Allen, New York, NY (US); Andrew Howland, New York, NY (US); Philip Beineke, Mountain View, CA (US); Mark Chandler, Atlantic Highlands, NJ (US); Michael Elashoff, Hillsborough, CA (US); Mladen Laudanovic, New York, NY (US); Jingshu Liu, Jersey City, NJ (US); Michael Cestone, Morristown, NJ (US); Jenny Liu, New York, NY (US)

(73) Assignee: Medidata Solutions, Inc., New York, NY (US)

( * ) Notice: Subject to any disclaimer, the term of this patent is extended or adjusted under 35 U.S.C. 154(b) by 261 days.

(21) Appl. No.: 15/443,828

(22) Filed: Feb. 27, 2017

(65) Prior Publication Data

US 2018/0246876 A1 Aug. 30, 2018

(51) Int. Cl.
*G16H 15/00* (2018.01)
*G06F 40/242* (2020.01)
(Continued)

(52) U.S. Cl.
CPC .......... *G06F 40/279* (2020.01); *G06F 40/242* (2020.01); *G06F 40/247* (2020.01); *G16H 15/00* (2018.01); *G16H 10/20* (2018.01)

(58) Field of Classification Search
CPC ............... G06F 19/326; G06F 17/2735; G06F 17/2765; G06F 17/2795
(Continued)

(56) References Cited

U.S. PATENT DOCUMENTS 5,251,131 A * 10/1993 Masand ................. G10L 15/18
704/9
8,255,347 B2 * 8/2012 Ellingsworth ........ G06F 16/313
706/20

(Continued)

*Primary Examiner* — Richemond Dorvil
*Assistant Examiner* — Rodrigo A Chavez
(74) *Attorney, Agent, or Firm* — Steptoe & Johnson LLP; Robert Greenfeld

(57) ABSTRACT

An apparatus for automatically mapping a verbatim narrative to a term in a medical terminology dictionary includes a natural language processor and a comparator. The natural language processor processes terms from the medical terminology dictionary and from a medical coding decision database to generate a processed database that also includes the original terms from the medical terminology dictionary and the medical coding decision database. The natural language processor also processes the verbatim narrative. The comparator compares the processed verbatim narrative to the terms in the processed database and determines whether the processed verbatim narrative is an exact match to a term in the processed database. The verbatim narrative is mapped to the term in the medical terminology dictionary that corresponds to the term in the processed database that is an exact match. The verbatim narratives may include adverse event narratives, concomitant medication narratives, or other types of narratives. A method for automatically mapping a verbatim narrative to a term in a medical terminology dictionary is also described and claimed.

24 Claims, 6 Drawing Sheets

(51) Int. Cl.
  *G06F 40/247*  (2020.01)
  *G06F 40/279*  (2020.01)
  *G16H 10/20*  (2018.01)

(58) Field of Classification Search
  USPC .......................................................... 704/9
  See application file for complete search history.

(56) References Cited

U.S. PATENT DOCUMENTS

| | | | |
|---|---|---|---|
| 8,620,842 B1* | 12/2013 | Cormack | G06F 16/285 |
| | | | 706/12 |
| 2008/0081955 A1* | 4/2008 | Eisenhandler | A61B 5/00 |
| | | | 600/300 |
| 2008/0249762 A1* | 10/2008 | Wang | G06F 40/30 |
| | | | 704/9 |
| 2009/0012842 A1* | 1/2009 | Srinivasan | G06F 40/30 |
| | | | 705/12 |
| 2010/0174528 A1* | 7/2010 | Oya | G06F 40/268 |
| | | | 704/10 |
| 2014/0058722 A1* | 2/2014 | Sun | G06F 40/284 |
| | | | 704/9 |
| 2014/0200914 A1* | 7/2014 | Rut | G16H 10/20 |
| | | | 705/2 |
| 2015/0379241 A1* | 12/2015 | Furst | G06F 40/247 |
| | | | 705/3 |
| 2017/0277736 A1* | 9/2017 | Sharma | G06F 16/2246 |
| 2018/0075011 A1* | 3/2018 | Allen | G06F 40/242 |
| 2018/0101598 A1* | 4/2018 | Allen | G06F 40/242 |
| 2018/0260426 A1* | 9/2018 | Sharifi Sedeh | G06F 16/35 |

* cited by examiner

APPARATUS AND METHOD FOR AUTOMATICALLY MAPPING VERBATIM NARRATIVES TO TERMS IN A TERMINOLOGY DICTIONARY

BACKGROUND

Clinical trials are used to determine whether a drug or device under test is safe and effective. One type of data that clinical trials collect is information about adverse events, which are any untoward medical occurrences experienced by a patient or clinical trial subject that may not necessarily have a causal relationship to the treatment being tested. These adverse events are often recorded using verbatim narratives that vary from person to person and from trial to trial. Another type of data that clinical trials collect is concomitant medications (often called "con-meds") narratives, which are descriptions of a drug or biological product, other than the drug under study, taken by a subject during the clinical trial.

Because one of the main purposes of a clinical trial is to test the safety of a drug or device, knowledge about con-meds and adverse events that are temporarily associated with the investigational treatment is very important, as is classifying the con-meds and adverse events. However, even though there are dictionaries that catalog con-meds and adverse events, mapping a verbatim narrative to a standardized term or entry in such a dictionary is not always performed in a consistent manner, resulting in incoherent analyses of the con-meds or adverse events.

Figure 1:
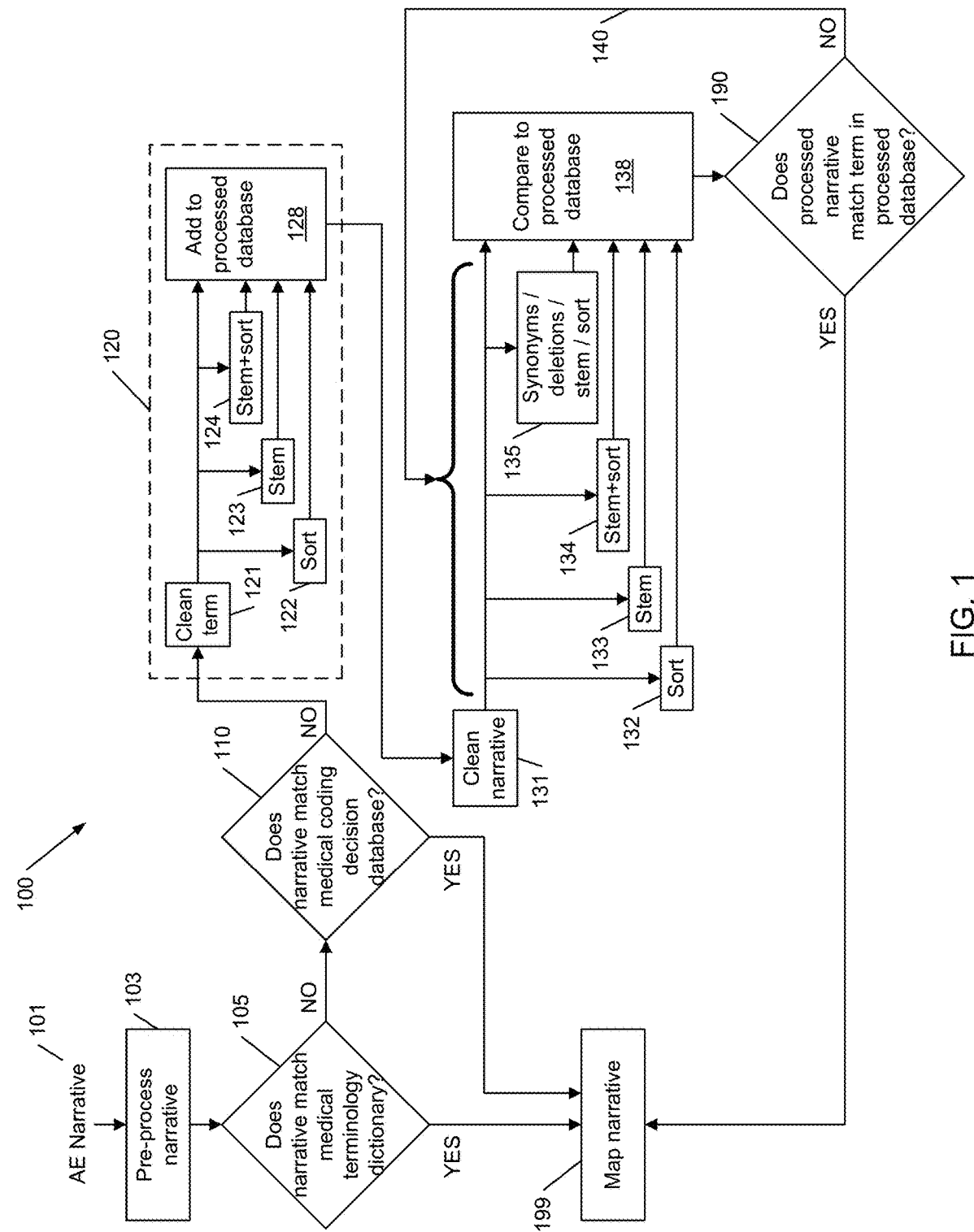
FIG. 1 is a flowchart showing a method for automatically mapping an adverse event narrative to a term in a medical terminology dictionary, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Many types of clinical trial data, such as blood pressure and heart rate, may be recorded as numbers, the range of which is often known very well. Such data may be tabulated and thereafter analyzed fairly easily to determine whether a drug is safe and effective. In contrast, an adverse event ("AE") that occurs during a clinical trial is generally recorded as a text or verbatim narrative, in a format that may differ from one recorder (e.g., patient, doctor, nurse, technician, etc.) to another and may even differ by the same recorder at a different time. Such differences may be as simple as spelling differences, which may be caused by typographical errors or that some words are spelled differently in different geographic areas. One example is "diarrhea," which may be misspelled (e.g., diarrea) or may be spelled differently in different countries (e.g., in the United Kingdom it is spelled "diarrhoea"). Other times, the same condition is described by its symptoms rather than a specific name. So "diarrhea" may be described as "loose stools," "Soft bowels," "soft stools," "Loose bowel movements," etc., and each of these words may be capitalized, may appear in singular or plural, or may be misspelled.

Similarly, con-med narratives may be recorded during a clinical trial to indicate medications other than the drug under test that the patient or subject is taking. Such narratives may include the brand name of the con-med, e.g., Lipitor®, the generic version of the drug or the active ingredient, e.g., atorvastatin, or a combination of one of these names with the salt or ester of the active ingredient, e.g., atorvastatin calcium. Sometimes, the drug name is accompanied by the dosage, e.g., 80 mg, and sometimes the drug delivery vehicle appears in the narrative, e.g., tablet.

There are currently standard dictionaries of terms for adverse events and drugs. The dictionary for adverse events, called the Medical Dictionary for Regulatory Activities (MedDRA®), is developed by the International Conference on Harmonisation of Technical Requirements for Registration of Pharmaceuticals for Human Use (ICH) and includes standard terminology for medical, health-related, and regulatory concepts pertaining to medical products for human use. MedDRA is arranged in a hierarchy of five levels—SOC (System Organ Class), HLGT (High Level Group Term), HLT (High Level Term), PT (Preferred Term), and LLT (Lowest Level Term). Of the five levels, PTs and LLTs are more relevant for the purposes of this patent application. A PT is a distinct descriptor (i.e., a single medical concept) for a symptom, sign, disease, diagnosis, therapeutic indication, investigation, surgical, or medical procedure, and medical, social, or family history characteristic. An LLT is generally more specific than a PT and is linked to only one PT. An LLT may be identical to the PT, a sub-element of the PT (e.g., PT "Contusion" and LLTs "Bruising of face" and "Bruising of leg"), a synonym (e.g., PT "Arthritis" and LLT "Joint inflammation") or a quasi-synonym (e.g., PT "Otitis externa" and LLT "Bilateral otitis externa") of the PT, or a lexical variant of the PT (e.g., PT "Acquired immunodeficiency syndrome" and LLT "AIDS"). An LLT may also be a more colloquial way of saying the PT (e.g., PT "Nasopharyngitis" and LLT "cold").

MedDRA includes about 75,000 unique LLTs and PTs. It is estimated that more than 10 million adverse event records have been collected over time using Medidata's clinical trial software. A human looking at these records may be able to standardize or map some of these millions of records to the 75,000 MedDRA terms. But that requires training, diligence, consistency, patience, time, and money. And if more than one person is used to standardize these records (which is very likely), differences between the people adds another chance for error or inconsistency.

Analogously, there is a dictionary for drugs, called the World Health Organization Drug Dictionary (WHODD or WHO Drug Dictionary), maintained by the Uppsala Monitoring Center. Like MedDRA, WHODD also includes a hierarchical classification system, which categorizes drugs according to the organ or system on which they act and their therapeutic, pharmacological, and chemical properties. Similar to the LLT in MedDRA, the WHODD's lowest level includes proprietary drug codes that identify the generic name or the trade name (TN), e.g., LIPITOR® or TYLENOL®. The proprietary drug code is an eleven-digit number that includes a six-digit "Drecno" (short for "Drug Record Number") for the active ingredient(s), a two-digit Sequence Number 1 identifying the salt or ester of the active ingredient, and a three-digit Sequence Number 2 identifying the trade name. For example, the Drecno 013261 is associated with the active ingredient atorvastatin. The drug code for generic atorvastatin is 013261 01 001 (which is the analog in WHODD to the Preferred Term in MedDRA) and the drug code for Lipitor is 013261 02 016. WHODD includes about 49,000 unique Drecnos.

It is often desirable to technically analyze the occurrences and types of adverse events and con-meds, for example, to better understand the effects of a drug or device under test. This analysis is often difficult, because adverse event and con-med narratives do not have standard formats. Attempts have been made to address the problem of analyzing unstructured narratives, for example by using a technical solution such as automating the standardization, coding, or mapping of these verbatim adverse event and con-med narratives to MedDRA terms or WHODD Drecnos. Medidata CODER®, an Internet-based enterprise coding solution, uses an auto-mapping algorithm based on exact string matching (i.e., if the AE narrative exactly matches the MedDRA term). This may work in about 60% of the adverse event narratives, but human intervention is needed to code the remaining 40% of the records. For con-med narratives, CODER will try to match the trade name or generic name and then map it to the corresponding drug code. This may work in less than about 60% of the con-med narratives. Below are examples of human-coded mappings from CODER:

| Verbatim | Assigned Term | Assigned Code | Drecno |
|---|---|---|---|
| atorvastatine | atorvastatin | 013261 01 001 | 013261 |
| atorvastatin | atorvastatin | 013261 01 001 | 013261 |
| Lipitor | atorvastatin | 013261 01 001 | 013261 |
| Lipitor 20 MG | Lipitor | 013261 01 014 | 013261 |
| Neustatin-A | Neustatin A | 013261 02 001 | 013261 |
| ES Tylenol | Tylenol Extra Strength | 000200 01 461 | 000200 |
| Tylenol | Tylenol/00020001/ | 000200 01 005 | 000200 |
| acetaminpohene | Acetaminophen | 000200 01 009 | 000200 |

Faced with this technical problem, the inventors have developed an improved system and method for standardizing, mapping, or coding the verbatim narratives that up until now have been coded by humans. This involves taking the verbatim narratives database and the mappings that have already been performed in CODER and technically processing the narratives using natural language processing and/or applying probabilistic models to the verbatim narratives.

Reference is now made to FIG. 1, which shows flowchart 100 comprising a method for automatically mapping an AE narrative to a term in a medical terminology dictionary, according to an embodiment of the present invention. In operation 103, AE narrative 101 may be pre-processed by removing capitalization, leading and trailing spaces, extra spaces (e.g., double spaces to single spaces), and/or surrounding quotation marks. (Pre-processing in this fashion may not be necessary at this point, but may be performed later as part of cleaning, as described below.) Operation 105 asks whether the pre-processed narrative matches a term in a medical terminology dictionary, such as MedDRA. A match may be determined using a hash table or a Python dictionary. If there is a match, then the narrative is mapped in operation 199 to that term. If not, then the system will search a medical coding decision database, such as Medidata CODER, in operation 110 and ask whether the pre-processed narrative matches a term in that database. A match here may also be determined using a hash table or Python dictionary. If there is a match, then since the medical coding decision database term already corresponds (or is already mapped) to a term in the medical terminology dictionary, AE narrative 101 can be mapped in operation 199 to the term in the medical terminology dictionary to which AE narrative 101 was most frequently mapped in the medical coding decision database.

If the pre-processed narrative does not match a term in the medical coding decision database (i.e., the answer to operation 110 is "NO"), then the system will begin natural language processing of the narrative to try to match it to a term in the medical terminology dictionary or medical coding decision database that has also been natural-language processed. One way of executing this is to create a "processed database" that includes versions of the terms in the medical terminology dictionary and medical coding decision database that have been processed to varying degrees. Such processing, shown in operation 120, may consist of cleaning, sorting, and stemming as described below.

In operation 121, the term may be cleaned. Cleaning may involve removing punctuation; removing numbers, measurements, and units such as: ×2, 2×2, #5, +2, 2+, 10, 5.25, (1), g, kg, mg, gm, gram, umol, mmol, kmol, ml, dl, /, %, percent, meter, m, mm, km, cm, lb, pound, in, inch, inches, feet, foot, ft, degree, °, ° C., ° F., cel, celsius, celcius, centigrade, fahrenheit, farenheit, hour, hr, h, minute, min, m, second, sec, s, bpm, etc.; removing stop words (common words that are often insignificant) such as: on, at, of, in, a, the, my, her, his, had, has, have, patient, etc.; and expanding abbreviations such as: r/t→related to, d/t→due to, l and lt→left, r and rt→right, b/l→bilateral, incr→increase, decr-→decrease, susp and sus→suspected, and abd and abdo-→abdominal. Cleaning may also include removing capitalization, leading and trailing spaces, extra spaces (e.g., double spaces to single spaces), and/or surrounding quotation marks, to the extent not already performed. The cleaned version of the term is then added to the processed database in operation 128. An example of a term in CODER that may be cleaned is "serum glucose (increase) 189 mg/dl." After cleaning, this becomes "serum glucose increase."

In operation 122, the cleaned term may be sorted and then added to the processed database in operation 128. Sorting involves normalizing the order of the words in the narrative. One type of normalization is putting the words in alphabetical order, but other sort orders may be used. Thus, sorting the cleaned term "serum glucose increase" alphabetically yields "glucose increase serum."

In operation 123, the cleaned term may be stemmed and then added to the processed database in operation 128. Stemming involves removing meaningless lexical variations, relative to the medical terminology dictionary. One method of stemming uses the Porter Algorithm, which involves (1) removing plurals and -ed or -ing suffixes; (2) changing a terminal y to an i when there is another vowel in the stem; (3) mapping double suffixes to single ones, e.g., -ization→-ize; -ational→-ate; -fulness→-ful; etc.; (4) removing suffixes, -ful, -ness etc.; (5) removing -al, -ant, -ence, etc.; and (6) removing a final -e. Examples of the results of the Porter Algorithm are "chest soreness" becomes "chest sore" and "colonic polyps" becomes "colon polyp." Using the previous example, stemming the cleaned term "serum glucose increase" yields "serum glucos increas."

In operation 124, the cleaned term may be stemmed AND then sorted and then added to the processed database in operation 128. Using the previous example, stemming and sorting the cleaned term "serum glucose increase" yields "glucos increas serum."

Performing operations 121-124 on the terms in the medical technology dictionary and medical coding decision database yields a processed database of alternative terms used for matching. Thus, using the previous example of CODER term "serum glucose (increase) 189 mg/dl," the terms "serum glucose increase," "glucose increase serum," "serum glucos increas," and "glucos increas serum" may be added to the processed database as related to "serum glucose (increase) 189 mg/dl." For completeness, the processed database may contain both the alternative versions created in operation 120 as well as the original terms from the medical terminology dictionary and medical coding decision database, because a processed narrative may match the original terms or the alternative versions. Moreover, because "serum glucose (increase) 189 mg/dl" has been assigned to the MedDRA term "blood glucose increased," the alternative versions may also be assigned to that MedDRA term.

Once the terms in the medical technology dictionary and medical coding decision database have been natural-language processed, the AE narrative (or the pre-processed narrative) may be subjected to a series of natural language processing operations itself. After each operation, the further processed narrative is compared to the processed database to determine if a match can be made, as described below.

In operation 131, the narrative may be cleaned in the same fashion the medical terminology dictionary or medical coding decision database term was cleaned in operation 121. The cleaned narrative may then be compared in operation 138 to the terms in the processed database. If there is a match in operation 190, then the process ends in operation 199 by mapping the narrative to the term in the medical terminology dictionary that corresponds to the matched term in the processed database. Thus, cleaning the narrative "Patient has a cold." yields "cold" (stop words "patient," "has," and "a" are removed, as is the period), which matches LLT "cold" in MedDRA.

If cleaning the narrative does not result in a match (arrow 140), then in operation 132 the cleaned narrative may be sorted in the same manner as in operation 122. The cleaned and sorted narrative may then be compared in operation 138 to the terms in the processed database. If there is a match in operation 190, then the process ends in operation 199 by mapping the narrative to the term in the medical terminology dictionary that corresponds to the matched term in the processed database. For example, pre-processing AE narrative "Unruptured cerebral aneurysm" yields "unruptured cerebral aneurysm," and sorting yields "aneurysm cerebral unruptured." This matches one of the processed terms for the MedDRA LLT "Aneurysm cerebral (unruptured)," which had been processed in operation 120 to yield the corresponding term "aneurysm cerebral unruptured" (pre-processing to remove capitals and cleaning to remove the parentheses). Thus the narrative "Unruptured cerebral aneurysm" may be mapped to "Aneurysm cerebral (unruptured)" in operation 199.

If cleaning and sorting the narrative does not result in a match (arrow 140), then in operation 133 the cleaned narrative may be stemmed in the same manner as in operation 123. The cleaned and stemmed narrative may then be compared in operation 138 to the terms in the processed database. If there is a match in operation 190, then the process ends in operation 199 by mapping the narrative to the term in the medical terminology dictionary that corresponds to the matched term in the processed database. For example, pre-processing AE narrative "ABDOMINAL BLOATNESS" yields "abdominal bloatness," sorting yields "abdominal bloatness" (no change), and stemming yields "abdomin bloat." This matches one of the processed terms for the MedDRA LLT "Abdominal bloating," which had been processed in operation 120 to yield the corresponding term "abdomin bloat" (pre-processing to remove capitals and stemming to remove the "al" and "ing"). Thus the narrative "ABDOMINAL BLOATNESS" may be mapped to "Abdominal bloating" in operation 199.

If cleaning and stemming the narrative does not result in a match (arrow 140), then in operation 134 the cleaned narrative may be stemmed and sorted in the same manner as in operation 124. The cleaned, stemmed, and sorted narrative may then be compared in operation 138 to the terms in the processed database. If there is a match in operation 190, then the process ends in operation 199 by mapping the narrative to the term in the medical terminology dictionary that corresponds to the matched term in the processed database. For example, pre-processing AE narrative "Enlarged Pituitary Gland" yields "enlarged pituitary gland," stemming produces "enlarg pituitari gland," and sorting produces "enlarg gland pituitari." This matches one of the processed terms for the MedDRA LLT "Pituitary gland enlargement," which had been processed in operation 120 to yield the corresponding term "enlarg gland pituitari" (pre-processing to remove capitals, stemming to change the "y" to an "i" and remove the "ement," and sorting to reorder the words alphabetically). Thus the narrative "Enlarged Pituitary Gland" may be mapped to "Pituitary gland enlargement" in operation 199.

If cleaning, sorting, stemming, and stemming+sorting do not result in a match, then in operation 135, the cleaned and stemmed narrative may be assigned stemmed synonyms or have terms deleted, followed by sorting if needed. Synonyms and deletions may be algorithmically derived from the medical coding decision database (e.g., Medidata CODER) to learn what words human CODER users consider to have the same meaning or are unnecessary, respectively. One way to determine synonyms and deletions is by taking the difference between the verbatim term and the term assigned by the human CODER users. In other words, synonyms and deletions may be determined by stripping whichever words are in common between the verbatim term and the assigned term. For example, if the verbatim narrative is "lower extremity edema" and the assigned term in CODER is "leg edema," stripping the common word "edema" leads to the synonym "lower extremity" for "leg." Other synonyms may include corrections for misspelled words, e.g., "heart" for "haert" or "increased" for "inceased." Similarly, if the verbatim narrative is "very tense" and the assigned term in CODER is "tense," stripping the common word "tense" leads to the conclusion that "very" is not relevant in some cases and can be discarded and considered a deletion word. Other possible deletion words may be "intermittent," "occasional," or "mild." All synonyms and deletions may be stemmed prior to use on the cleaned and stemmed verbatim narratives in operation 135.

One algorithm that may be used to determine synonyms and deletions is as follows:
  a. Tokenize the cleaned and stemmed narrative. "Tokenizing" means reducing a string to a list of words. For example, the cleaned and stemmed narrative "skin thicken inject site" would become the following list of tokens: ["skin," "thicken," "inject," "site" ];
  b. For each token $t_i$ in $t_1 \ldots t_n$, e.g., ["skin," "thicken," "inject," "site" ], look up $t_i$ in the list of synonyms and deletions:
    i. If $t_i$ exists, replace it with the first synonym or delete it. Then sort and check for a match in MedDRA. If a match exists, output;
    ii. If another synonym exists for $t_i$, replace it again or delete it. Then sort and check again for a match in MedDRA. If a match exists, output;
    iii. Repeat for $t_{i+1} \ldots t_n$.
  In the above example, no matches are found in this step.
  c. Repeat step b for each token plus its neighbor, e.g., ["skin thicken," "thicken inject," "inject site" ];
  In the above example, no outputs are produced from this step.
  d. Repeat step b for each token plus its two following neighbors, e.g., ["skin thicken inject," "thicken inject site" ];
  In the above example, no matches are found in this step.
  e. Next, swap out tokens separated by another token. For each token in $t_1 \ldots t_n$, e.g., ["skin," "thicken," "inject," "site" ], look up $t_i$ in the list of synonyms and deletions:
    i. If $t_i$ exists, replace it with the first synonym or delete it. For example, "skin" is deleted resulting in the following list of tokens: [" ", "thicken," "inject," "site" ].
    ii. For each token in $t_{i+1} \ldots t_n$, e.g., ["thicken," "inject," "site" ], look up $t_j$ in the list of synonyms and deletions:
      If $t_j$ exists, replace it with the first synonym or delete it. Then sort and check for match in MedDRA. If a match exists, output. For example, replacing the word "thicken" with the synonym "fibrosi" produces the following list of tokens: [" ", "fibrosi," "inject," "site" ]. Sorting has no effect, and the concatenation of the list of strings produces "fibrosi inject site," which matches the cleaned, stemmed, and sorted MedDRA term "injection site fibrosis" (i.e., "fibrosi inject site").
      If another synonym or deletion exists for the same token, replace it again or delete it. Then sort and check again for a match in MedDRA. If a match exists, output. For example, the token "thicken" can also be replaced with the synonym "calcif," producing the following list of tokens: [" ", "calcif," "inject," "site" ]. Again, sorting has no effect, and the concatenation of the list of strings produces "calcif inject site," which matches the cleaned, stemmed, and sorted MedDRA term "injection site calcification" (i.e., "calcif inject site"). The token "thicken" can also be replaced with "hypertrophi" or "sclerosi" to find a match in MedDRA.
      Repeat for $t_{i+2}$. In the example provided, no other matches are found by replacing "inject" or "site" when "skin" has been deleted;
    iii. If another synonym exists for $t_i$, replace it again and repeat step ii. In the example provided, no matches are found when "skin" is replaced with a synonym.
  f. Of all "synonymous" verbatim narratives that found a match in the steps above, select the one that is associated with the highest CODER edit rate, i.e., the one that uses synonyms or deletions that are most frequently observed in CODER (i.e., weighted by its observed frequency). This can be calculated according to the following equation:

$$\omega = \frac{\text{\# of times the synonym or deletion is observed in CODER}}{\text{\# of times the original word or phrase is observed in CODER}}$$

Note that for matches from Step e. where more than one synonym or deletion has been used, the average CODER edit rate is calculated. An example of this weight calculation is as follows: if "skin" is observed in 10 terms in the CODER database, and 5 of those terms are associated with a MedDRA dictionary term that does not contain "skin," then the average CODER edit rate for the deletion of "skin" would be 50%. In the example provided, "fibrosi inject site" is associated with the highest average CODER edit rate and thus the associated MedDRA term is assigned.

An example showing operations 131-135 is the mapping of the verbatim narrative "SKIN THICKENING AT INJECTION SITE." Pre-processing the narrative in operation 103 yields "skin thickening at injection site," which is not a match. Cleaning in operation 131 yields "skin thickening injection site," and sorting the cleaned narrative in operation 132 yields "injection site skin thickening," neither of which is a match. Stemming the cleaned narrative in operation 133 produces "skin thicken inject site," which is not a match. Stemming+sorting the cleaned narrative in operation 134 produces "inject site skin thicken," which is still not mappable to MedDRA or CODER. Returning to the cleaned and stemmed narrative (output of operation 133) "skin thicken inject site," substituting in operation 135 the stemmed synonym "fibrosi" (i.e., root of "fibrosis") for "skin thicken" yields "fibrosi inject site." Sorting has no effect. This matches one of the processed terms for the MedDRA LLT "Fibrosis injection site," which had been processed in operation 120 to yield the corresponding term "fibrosi inject site" (pre-processing to remove capitals, stemming to remove the "s" and "ion"). Thus the narrative "SKIN THICKENING AT INJECTION SITE" may be mapped to "Fibrosis injection site" in operation 199.

Besides the operations shown in FIG. 1, other operations or series of operations may be used to automatically map a verbatim narrative to a term in a terminology dictionary. As stated above, pre-processing operation 103 may be performed as part of the cleaning operations (e.g., operation 131) rather than at the beginning. In addition, not every one of operations 131 to 135 needs to be used to map a narrative. As was discussed, the narrative may be mapped after one or two or three of the operations. Also, processing operation 120 (to develop the processed database) may be performed all at once on both the medical terminology dictionary and the medical coding decision database or it may be performed in stages (e.g., clean the database terms, then clean the narrative, then compare the cleaned narrative to the cleaned database terms, and, if no match, then go to the sorting steps, etc.). In some embodiments, to save processing time and power, the order of the operations may be important—cleaning, then sorting, then stemming and sorting, then applying synonyms and deletions. In other embodiments, the actual order of the operations in the flowchart may not be critical.

In some embodiments, splitting may be used as another natural language processing operation. This may occur if two or more adverse events are reported in the same string. In that case, the two (or more) verbatim narratives may be split on the following punctuation marks: ; –, ([+and the following terms: secondary to, due to, related to, and, with. Each split may then be cleaned as previously described. Some examples of verbatim narratives (left) that have been mapped to MedDRA terms (right) via splitting are:

abdominal cramping and bloating→abdominal cramp, bloating
tooth infection (root canal)→tooth infection, root canal
hematoma right hip (after fall)→hematoma, fall
((right leg pain)) secondary to fracture→leg pain, fracture
headache, vomit→headache, vomiting
lower gi bleed, coumadin toxicity, "deconditioned state"→gi bleed, drug toxicity, general physical health deterioration
skin dryness/puffiness around eyes→dry skin, tissue puffing
indigestion with heartburn→indigestion, heartburn
general deterioration with weakness, fatigue, dizziness, nausea→general physical health deterioration, weakness, fatigue, dizziness, nausea In a further embodiment, splitting may be performed on the front end by the user instead of after operation 131.

Testing by the inventors on AE narratives has been favorable. The performance was evaluated on a validation set consisting of 227 clinical studies with 64,042 verbatim adverse event narratives where the MedDRA (human) coding was hidden. This set comprised 22,267 unique validation verbatim adverse event narratives. The coverage rate, which is the percent of verbatim adverse event narratives auto mapped to MedDRA, was 95.8%. This compares to about 60% for the CODER algorithm. The accuracy rate, which is the percent of mapped terms that agree with the MedDRA term, was 97.2%. This compares to 96.3% for human coders at drug sponsors. These reported rates are based on a 5% trimmed mean over all studies. The speed at which a single verbatim narrative was mapped to MedDRA was 4 milliseconds on average, using multiprocessing. This performance was consistent across drug sponsors and various study-level features, including therapeutic area, clinical trial phase, and medical indication.

Figure 2A:
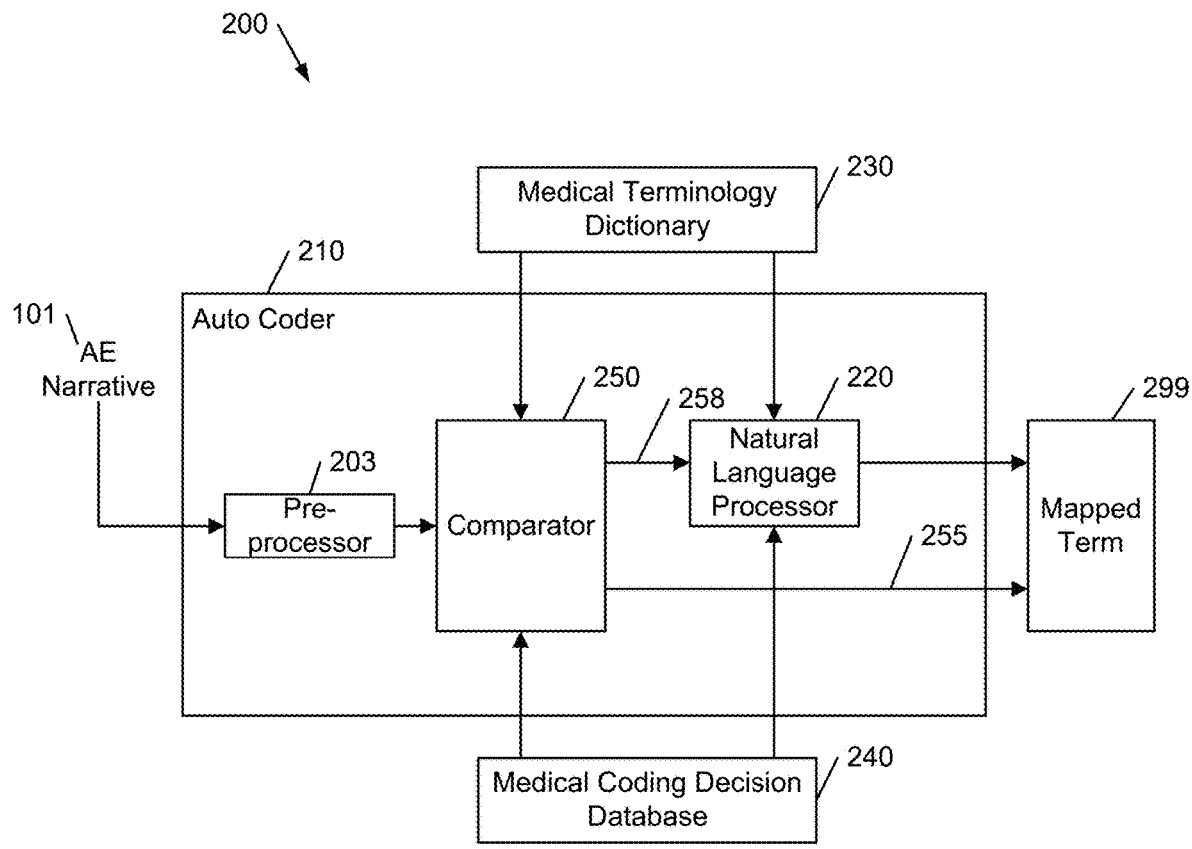
FIG. 2A is a block diagram of a system for automatically mapping an adverse event narrative to a term in a medical terminology dictionary, according to an embodiment of the present invention.

Reference is made to FIG. 2A, which is a block diagram of a system 200 for automatically mapping an adverse event narrative to a term in a medical terminology dictionary, according to an embodiment of the present invention. System 200 comprises auto coder 210, medical terminology dictionary 230, and medical coding decision database 240. Auto coder 210 includes pre-processor 203, natural language processor 220, and comparator 250. Auto coder 210 takes AE narrative 101 and produces a mapped term 299, using terms or entries from medical terminology dictionary 230 and medical coding decision database 240. Comparator 250 is used to determine if AE narrative 101 (processed via pre-processor 203 to remove capitals, leading and trailing spaces, multiple spaces, and/or surrounding quotation marks) matches a term in medical terminology dictionary 230. Such comparison may be made using a hash table or Python dictionary. If such a match can be made, the term is output via arrow 255 as mapped term 299. If such a match cannot be made, comparator 250 may be used to determine if the pre-processed narrative matches a term in medical coding decision database 240. If such a match can be made (again using a hash table or Python dictionary, for example), the term in medical terminology dictionary 230 that corresponds (or is already mapped) to the term in medical coding decision database 240 is output via arrow 255 as mapped term 299. If this match cannot be made, the (pre-processed) AE narrative may be further processed using natural language processor 220 via arrow 258, as was described in relation to flowchart 100. An example of medical terminology dictionary 230 is MedDRA, and an example of medical coding decision database 240 is Medidata CODER.

Figure 2B:
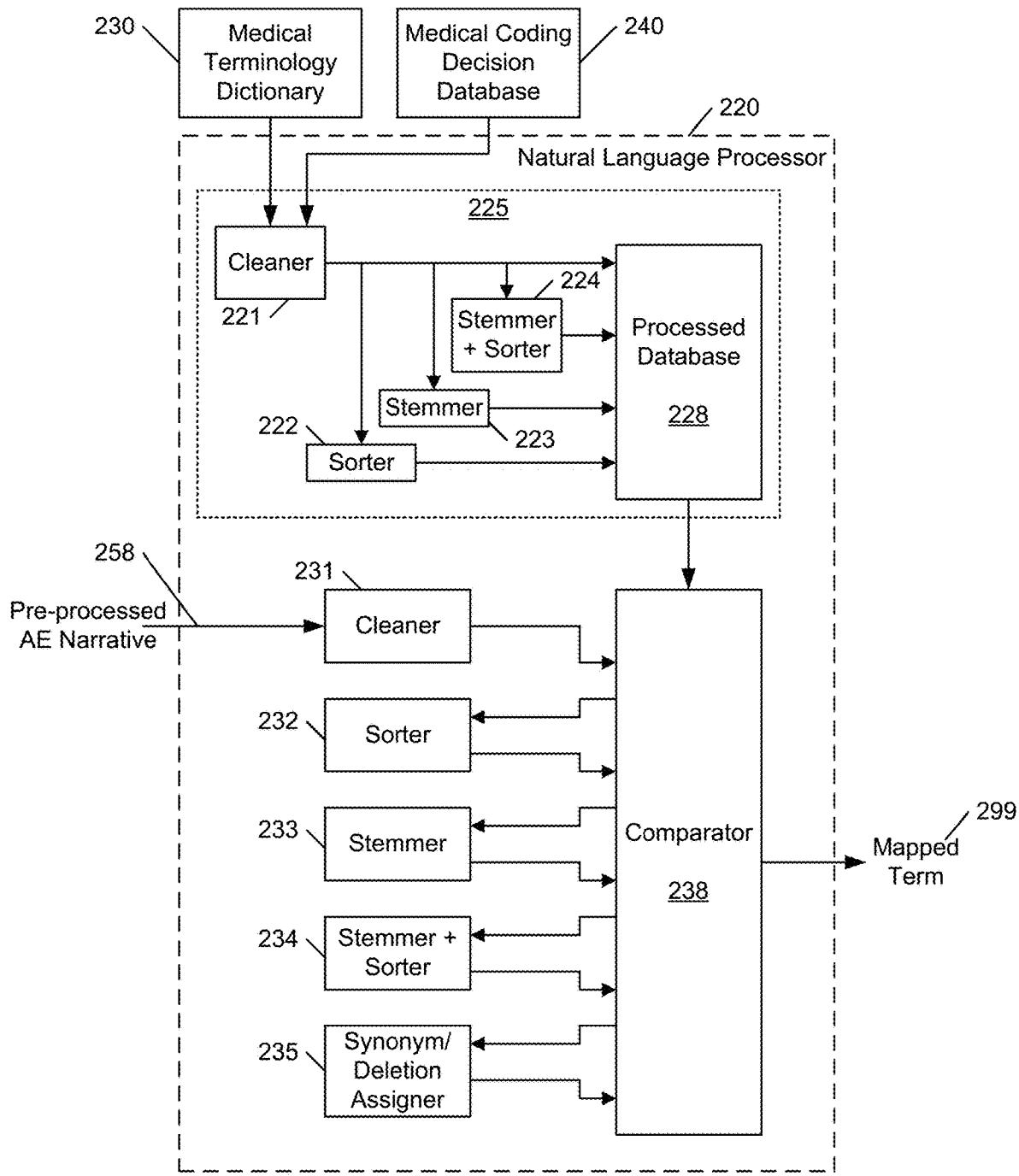
FIG. 2B is a block diagram of the natural language processor of FIG. 2A, according to an embodiment of the present invention.

FIG. 2B is a block diagram of natural language processor 220, according to an embodiment of the present invention. Natural language processor 220 has two main functions: (1) processing terms in medical terminology dictionary 230 and medical coding decision database 240 to produce a processed database and (2) processing the narrative in a variety of ways and comparing the results with terms in the processed database. The first processing function occurs in term processor 225, which includes cleaner 221, sorter 222, stemmer 223, stemmer+sorter 224, and processed database 228. The second processing function uses cleaner 231, sorter 232, stemmer 233, stemmer+sorter 234, and synonym/deletion assigner 235 (collectively called "subprocessors").

Processing terms using term processor 225 includes cleaning the medical terminology dictionary and medical coding decision database terms in cleaner 221 as described above with respect to operation 121 and adding the cleaned terms to processed database 228. The cleaned terms may be sorted using sorter 222 as in operation 122, and the sorted, cleaned terms may be added to processed database 228. The cleaned terms may also be stemmed using stemmer 223 as in operation 123, and the stemmed, cleaned terms may be added to processed database 228. Finally, the cleaned terms may be stemmed+sorted using stemmer+sorter 224 as in operation 124, and the stemmed+sorted and cleaned terms may be added to processed database 228. Processed database 228 thus includes alternative versions of original terms in the medical terminology dictionary and medical coding decision database and, for completeness, may contain the original terms themselves to facilitate matching to processed narratives.

Such matching may occur as follows. After AE narrative 101 is pre-processed in pre-processor 203 (FIG. 2A) to remove capitals, leading and trailing spaces, multiple spaces, and/or surrounding quotation marks, the narrative may be input to cleaner 231 via arrow 258 and cleaned as described above with respect to operation 131. The cleaned narrative may then be compared using comparator 238 to the terms in processed database 228. If there is a match, comparator 238 outputs mapped term 299. If there is no match, the cleaned narrative goes through the other subprocessors -sorter 232, stemmer 233, stemmer+sorter 234, and synonym/deletion assigner 235. The functions of these subprocessors were described above with respect to operations 132-135, respectively. The output of each subprocessor may be compared using comparator 238 to the terms in processed database 228. If there is a match, comparator 238 outputs mapped term 299. If there is no match in one subprocessor, then the cleaned narrative proceeds to the next subprocessor to see if there is a match, in which case comparator 238 outputs mapped term 299.

The parts and blocks shown in FIGS. 2A and 2B are examples of parts that may comprise system 200 and natural language processor 220 and do not limit the parts or modules that may be included in or connected to or associated with these systems and their components. Pre-processor 203 may not be used prior to comparator 250 and instead may be part of cleaner 231. As stated above, natural language processor 220 may not be needed in certain operations, or may just be used to generate the processed database. Similarly, not all of the subprocessors may be needed to map the AE narrative to mapped term 299. Also, while two comparators 250 and 238 are shown in FIGS. 2A and 2B, there may only be a single comparator used in both the auto coder and the natural language processor. Moreover, while comparator 238 is shown in FIG. 2B as being part of natural language processor 220, comparator 238 may be a separate component. In addition, a comparator may include a module that performs comparisons, and other modules may select a term that is a match and map the narrative to the mapped term. The blocks shown within the dashed lines of natural language processor 220 may reside in different physical "boxes" or devices, and the connections between them may be wired or wireless, via physically close connections or over a network.

Figure 3A:
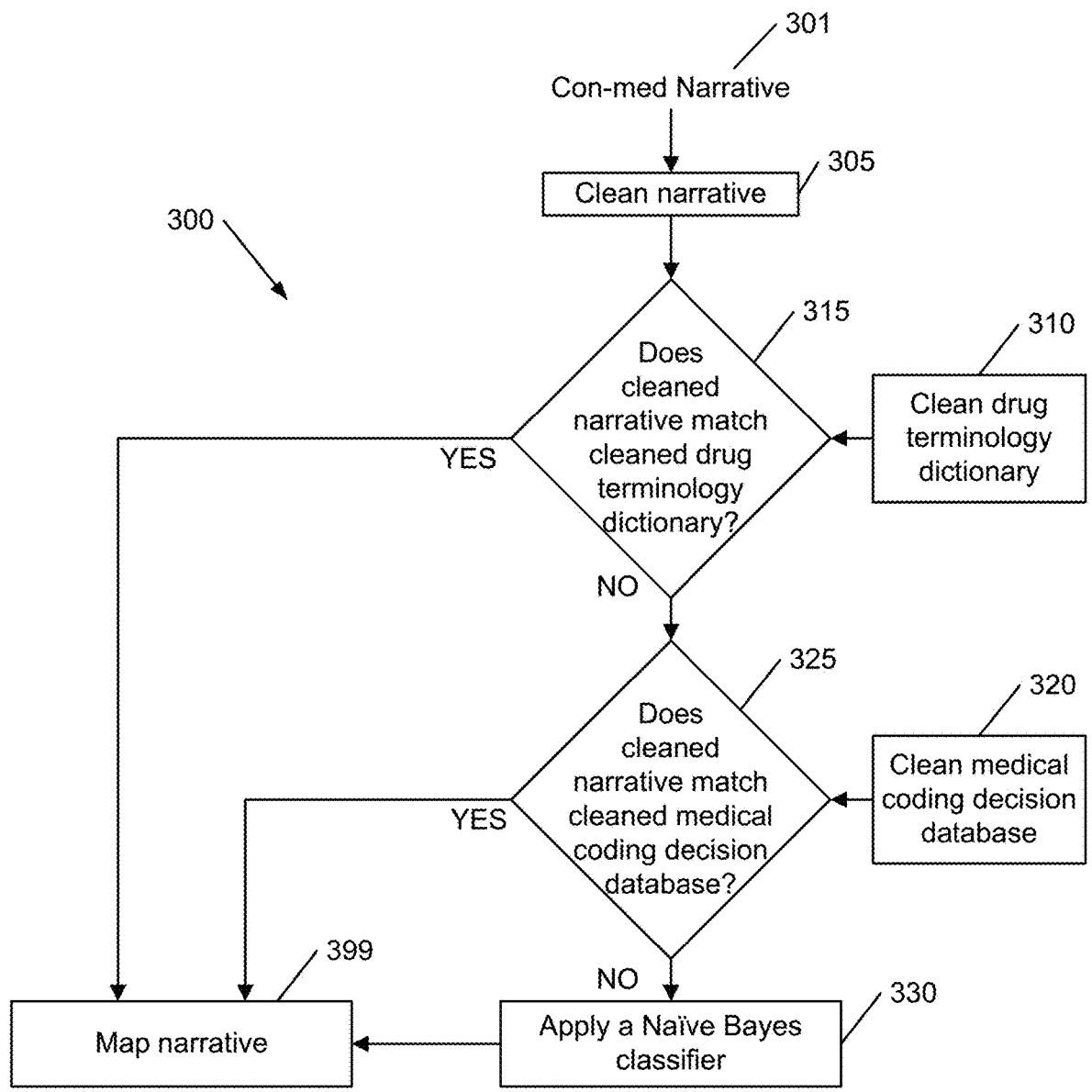
FIGS. 3A and 3B are flowcharts showing methods for automatically mapping a con-med narrative to a term in a drug terminology dictionary, according to embodiments of the present invention.
Figure 3B:
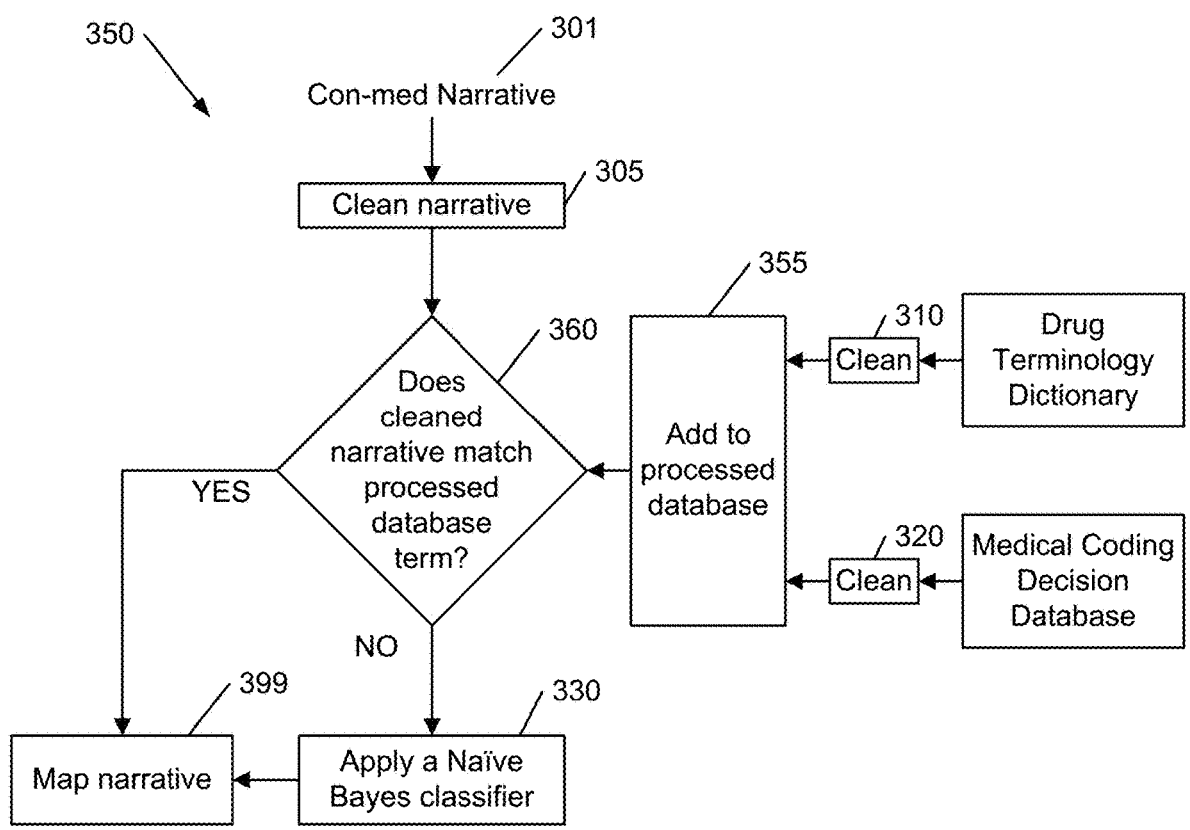

Reference is now made to FIGS. 3A and 3B, which are flowcharts 300, 350 showing methods for automatically mapping a con-med narrative to a term in a drug terminology dictionary, according to embodiments of the present invention.

In operation 305, con-med narrative 301 may be cleaned by removing leading and trailing spaces, multiple spaces, and single and double quotation marks and making all verbatim narratives lower case. In operation 310, the entries in the drug terminology dictionary, such as WHODD, may be cleaned in the same way (drug trade names are often partially or fully capitalized, so cleaning normalizes these variations). Operation 315 asks whether the cleaned narrative matches a term in the cleaned drug terminology dictionary, such as an active ingredient or a trade name. As with the AE narratives, a match may be determined using a hash table or a Python dictionary. If there is a match to an active ingredient, then the narrative is mapped in operation 399 to that term (or to the Drecno associated with the active ingredient). If there is a match to a drug trade name, then the narrative is mapped to the active ingredient or Drecno that corresponds to the trade name (e.g., atorvastatin for Lipitor®).

If there is no match, then in operation 320, the entries in a medical coding decision database, such as Medidata CODER, may be cleaned in the same way that the WHODD terms were cleaned. The system will then search the medical coding decision database in operation 325 and ask whether the cleaned con-med narrative matches a term (active ingredient or drug trade name) in the cleaned medical coding decision database. A match here may also be determined using a hash table or Python dictionary. If there is a match, then since the medical coding decision database term already corresponds (or is already mapped) to a term in the drug terminology dictionary, con-med narrative 301 can be mapped in operation 399 to the term (e.g., active ingredient or Drecno) in the drug terminology dictionary to which con-med narrative 301 was most frequently mapped in the medical coding decision database. The cleaning steps in operations 310, 320 (and possibly 305) may be considered to be a type of natural language processing as described in the text accompanying FIG. 1.

Instead of performing operations 310 and 320 in the order shown in FIG. 3A, FIG. 3B shows that both the drug terminology and the medical coding decision databases may be cleaned and the cleaned terms added to a processed database in operation 355, and the cleaned terms may be associated with an active ingredient or Drecno from the drug terminology dictionary. Then there may be a need for only a single matching operation, such as operation 360, instead of operations 315 and 325, in which the cleaned narrative is matched against a term in the processed database. If so, then con-med narrative 301 may be mapped to the active ingredient or Drecno that corresponds to such term.

In developing this invention, the inventors have processed the con-med data from Medidata CODER as follows. The raw CODER data included over 3.4 million con-med observations from nearly 1100 clinical studies. The data are then split into two subsets—a training set and a validation set. The training set contains approximately 2.21 million observations (approximately ⅔ of the observations) from 786 studies and the validation set includes approximately 1.10 million observations from 260 studies.

Within the Medidata CODER training set the mappings from con-med narratives to Drecnos exhibit a high degree of consistency among different (human) coders, especially for narratives that occur most frequently. So, there is confidence that the assigned Drecnos provide an accurate "ground truth" against which to benchmark standardization methods. For narratives that have been assigned to multiple Drecnos, however, another method is needed to resolve conflicting mappings. For these narratives, the Drecno that is selected is the one that was assigned in the plurality of the mappings. If there is more than one mapping that meets this criterion (i.e., if there is a "tie" between mappings), a weight is assigned that is inversely proportional to the number of ways the tie was split. For example, mappings for narratives with a two-way tie would receive each receive a 50 percent weight when evaluating accuracy.

However, the Drecnos with a plurality of mappings may still be incorrect, especially for narratives that occur infrequently. Since fewer coders have encountered these narratives, any one coder's mapping decision carries greater influence. These observations necessarily comprise a small portion of the dataset and hence likely have a limited impact. For example, narratives that occur 10 or fewer times represent less than one percent of the training data. In addition, narratives for drugs with ambiguous trade names can be assigned to two or more Drecnos, each of which is plausibly correct. Choosing the Drecno with a plurality of mappings in these situations potentially biases statistics evaluating the accuracy of standardization techniques. The inventors determined that disagreement was most prevalent among infrequently occurring narratives and nearly non-existent among narratives that occur very frequently. Accordingly, any bias introduced from ambiguous trade names is likely very limited.

As stated above, one way of mapping in operation 399 in the situation in which the narrative matches the medical coding decision database is to assign the Drecno that was selected for a plurality of observations in the training data set. In the event of a tie, the method described above could be used. Alternatively, in the event of a tie, a Drecno may not be assigned and mapping may be deferred to operation 330.

Thus, if con-med narrative 301 does not match a term in the medical coding decision database (i.e., the answer to operation 325 is "NO") or if there is a tie among more than one Drecno, then the system will apply a probabilistic model to con-med narrative 301. In operation 330, such probabilistic model may be a Naïve Bayes classifier or model. Three types of Naïve Bayes classifiers are described with respect to operation 330, Naïve Bayes with Words; Naïve Bayes with n-Grams of Letters; and Naïve Bayes with Priors, but other classifiers may also be used.

The Naïve Bayes classifier is a model known for its simplicity, scalability, and predictive power. In the Naïve Bayes Model with Words, feature vectors of word frequencies are constructed and it is assumed that the class conditional features follow a multinomial distribution. Features are assumed to be independent conditional on the class, and the Drecno is selected that maximizes the posterior distribution. If $x_i$ is the frequency of the $i^{th}$ feature in a new narrative (one that does not appear in the CODER training set), then the narratives are classified according to:

$$\hat{y} = \underset{k \in 1, 2, \ldots K}{\arg\max} \, p(C_k) \frac{\left(\sum_i x_i\right)!}{\prod_i x_i!} \prod_i p_{ik}^{x_i}$$

$$= \underset{k \in 1, 2, \ldots K}{\arg\max} \, p(C_k) \prod_i p_{ik}^{x_i}$$

$$= \underset{k \in 1, 2, \ldots K}{\arg\max} \, p(C_k) \prod_i \left[\frac{N_{ik} + 1}{N_k + |V|}\right]^{x_i}$$

where $N_{ik}$ is the number of times the $i^{th}$ feature occurs in class k in the training set, $N_k = \Sigma_{j \in k} N_{jk}$ is the sum of all feature frequencies in class k, and $|V|$ is the number of unique features in the training set. This model may be estimated with Laplace smoothing to allow the assignment of non-zero probabilities to features not observed in the training set. (This equation is applicable to all the Naïve Bayes models, not just Naïve Bayes with Words.)

This model adds flexibility to the CODER mappings in two ways. First, term-frequency feature vectors are agnostic to the order of the words in the verbatim. For example, Bayer Extra Strength and Extra Strength Bayer are treated as two distinct narratives by the CODER mapping method, but are represented by identical feature vectors. Second, a probabilistic approach is more robust to the presence of extraneous information, such as prescribed dosages. So long as the contribution to the likelihood from words related to the drug outweighs contributions related to extraneous information, the estimated model should select the correct class more often than not. In fact, if certain drugs tend to be prescribed in consistent dosages, the extraneous information may even help identify the correct class.

This model may be tuned by specifying the minimum number of times a feature must appear before it is included in the model. For example, if the feature need only appear once, the error rate may be as much as 18%, but if the feature appears a minimum of five times to be included in the model, the error rate decreases to about 15.5%. A value of 12 (i.e., if the feature appears a minimum of 12 times) minimizes the error rate at just under 15%.

Similar to the CODER mappings, the Naïve Bayes with Words for features requires an exact match to words contained in narratives in the training. So, narratives that contain words that are misspelled in ways not observed in the training data may not be matched. For example, atorvastatin may be misspelled as atorvastatine, atrovastatin, atorvastatina, atorvastatinum, etc. The second model, the Naïve Bayes Model with n-Grams of Letters, addresses the misspelling issues by identifying the portions of narratives that are in common with each other.

To do this, n-Grams of letters are extracted from words in the con-med narratives. For example, extracting 4-grams from the narrative atorvastatin yields the following list of partial features: ATOR, TORT, ORVA, RVAS, VAST, ASTA, STAT, TATI, ATIN. The table below shows partial feature vectors for several misspellings of atorvastatin. There is one column for each 4-gram extracted from the correctly-spelled narrative atorvastatin, where ones and zeros indicate whether the misspelled narrative has a given feature in common with the correctly spelled narrative. Overall, there is a large degree of similarity across misspellings, indicated by the lack of cells with a zero.

| Narrative | ATOR | TORV | ORVA | RVAS | VAST | ASTA | STAT | TATI | ATIN |
|---|---|---|---|---|---|---|---|---|---|
| atorvastatine | 1 | 1 | 1 | 1 | 1 | 1 | 1 | 1 | 1 |
| atrovastatin | 0 | 0 | 0 | 0 | 1 | 1 | 1 | 1 | 1 |
| atorvastatinum | 1 | 1 | 1 | 1 | 1 | 1 | 1 | 1 | 1 |
| atorvastastin | 1 | 1 | 1 | 1 | 1 | 1 | 0 | 0 | 0 |
| atorvostatin | 1 | 1 | 0 | 0 | 0 | 0 | 1 | 1 | 1 |
| atorvast[at]in | 1 | 1 | 1 | 1 | 1 | 0 | 0 | 0 | 0 |
| atorvastatina | 1 | 1 | 1 | 1 | 1 | 1 | 1 | 1 | 1 |
| atorvasterol | 1 | 1 | 1 | 1 | 1 | 0 | 0 | 0 | 0 |
| ato[r]vastatin | 0 | 0 | 0 | 0 | 1 | 1 | 1 | 1 | 1 |
| atorvast[a]stin | 1 | 1 | 1 | 1 | 1 | 0 | 0 | 0 | 0 |

Besides 4-grams, the model may use features having any letter-length of 2 or more. The 2-gram model yielded an error rate of over 13 percent, whereas the 3-gram model yielded an error rate of a little over 10%, the 4-gram model yielded an error rate of about 8.7%, and the 5-gram model yielded an error rate of a little over 9%, with longer feature-length models having even higher error rates. Thus, a 4-gram model yielded the lowest error rate, which is over 6% better than the words-based model. (The inventors selected a parameter of 15 for the minimum number of times a feature must appear before it is included in the model (as discussed above with respect to the words-based model), because more pruning reduces the number of model parameters without having a deleterious effect on the error rate.)

The above models are best suited for classifying new narratives that are similar to the narratives observed in historical CODER data; however, not all drugs are contained in the historical data, including (1) drugs with new trade names that are not observed in the historical data but share the same active ingredient(s) as other drugs that are observed in the historical data and (2) drugs that have entirely new active ingredient(s).

So, the third model, Naïve Bayes with Priors may be used. In this model, for the first group of drugs, the WHO Drug Dictionary can be used to identify all of the trade names associated with the subset of Drecnos that are observed in the historical CODER data. This information may be incorporated into the Naïve Bayes models by augmenting the CODER training data with observations from the WHO Drug Dictionary where the WHO Drug drug name is inputted as a new narrative. Conceptually, this approach is equivalent to introducing Dirichlet priors on both the class probabilities and the class-conditional feature probabilities. The weight on these priors may be increased by introducing multiple iterations of the observations from the WHO Drug Dictionary. Both the words-based model and the letters-based model benefit from such multiple iterations—with the words-based model benefiting more (reducing the error rate by almost two percentage points) with 14 iterations and the letter-based model improving by 0.8% (from 8.7 to 7.9%) when 10 iterations are included. Such an approach may also be used for the second group of drugs, those that have entirely new active ingredient(s), although it may increase the complexity of the classification task, since there are 8,917 unique Drecnos in the CODER data and 49,242 potential Drecnos to choose from in the complete WHO Drug Dictionary.

A further modification of the Naïve Bayes models may include using the words-based model in some cases and the letters-based model in others. More specifically, if the probability of the assigned Drecno exceeds a certain value from 0 to 1, the words-based model would be used, otherwise the letters-based model would be used. The error rate of this combined model is minimized when the value equals 0.63; thus, the words-based model would be used if the probability of the assigned class exceeds 0.63, and the letters-based model would be used the rest of the time. This reduced the error rate from 7.9% to 7.7%.

The letters-based Naïve Bayes model may be combined with previous mappings from CODER to improve the error rates of both approaches. For narratives that were observed in the training data, this combined approach has an error rate of 0.6%; for narratives that were not observed in the training data, the combined approach has an error rate of 35.8%. Together, the error rate over the whole validation set is 3.7%, compared to 7.9% for the letters-based Naïve Bayes model and 10.9% for the CODER mappings.

Besides the operations shown in FIGS. 3A and 3B, other operations or series of operations may be used to automatically map a con-med narrative to an active ingredient in a terminology dictionary. For example, operation 325 may not be used -just the probabilistic model in operation 330 may be sufficient to map the narrative with a low error rate. Moreover, the actual order of the operations in the flowchart may not be critical.

Figure 4:
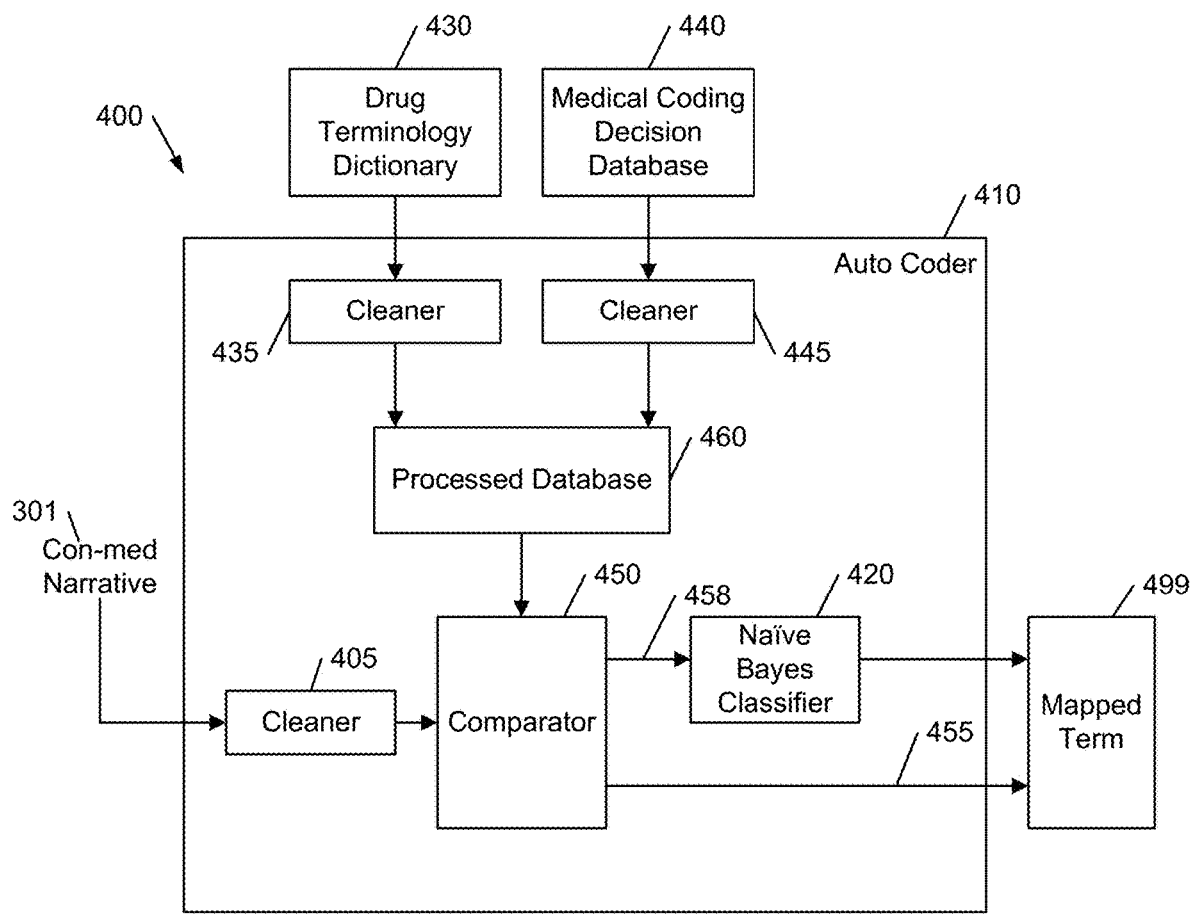
FIG. 4 is a block diagram of a system for automatically mapping a con-med narrative to a term in a drug terminology dictionary, according to an embodiment of the present invention.

Reference is now made to FIG. 4, which is a block diagram of a system 400 for automatically mapping a con-med narrative to a term in a drug terminology dictionary, according to an embodiment of the present invention. System 400 comprises auto coder 410, drug terminology dictionary 430, and medical coding decision database 440. Auto coder 410 includes cleaners 405, 435, 445, processed database 460, naïve Bayes classifier 420, and comparator 450. Auto coder 410 takes con-med narrative 301 and produces a mapped term 499, using terms or entries from drug terminology dictionary 430 and medical coding decision database 440. Cleaners 435, 445 are used to clean (as described above with respect to operations 310, 320) terms in drug terminology dictionary 430 and medical coding decision database 440. Cleaners 435, 445 (and possibly 405) may be considered to be a type of natural language processor as described in FIGS. 2A and 2B. The cleaned terms are then added to processed database 460. Comparator 450 is then used to determine if con-med narrative 301 (cleaned via cleaner 405) matches a term from processed database 460. Such comparison may be made using a hash table or Python dictionary. If such a match can be made, the term is output via arrow 455 as mapped term 499. If this match cannot be made, the cleaned con-med narrative may be input to naïve Bayes classifier 420 via arrow 458, as was described in relation to flowcharts 300 and 350. The naïve Bayes classifier used may be any of the models described above. An example of drug terminology dictionary 430 is WHODD, and an example of medical coding decision database 440 is Medidata CODER.

The parts and blocks shown in FIG. 4 are examples of parts that may comprise system 400 and do not limit the parts or modules that may be included in or connected to or associated with this system and its components. While three cleaners 405, 435, 445 are shown, there may only be a single cleaner (or natural language processor) used for such operation. The blocks shown in auto coder 410 may reside in different physical "boxes" or devices, and the connections between them may be wired or wireless, via physically close connections or over a network.

One benefit of the present invention is that it automatically maps adverse event and con-med narratives to terms in the medical terminology and drug dictionaries and does so more accurately than a person can and much more quickly. The invention also provides more coverage and a lower error rate than using the medical coding decision database by itself. This leads to the production of more accurate reports from a clinical trial to a regulatory agency describing the safety of a drug or device being tested in the trial. It also allows sponsors or others to perform more robust statistical analyses involving adverse events and con-meds.

Aspects of the present invention may be embodied in the form of a system, a computer program product, or a method. Similarly, aspects of the present invention may be embodied as hardware, software or a combination of both. The system may provide a cloud service. Aspects of the present invention may be embodied as a computer program product saved on one or more computer-readable media in the form of computer-readable program code embodied thereon.

For example, the computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Computer program code in embodiments of the present invention may be written in any suitable programming language. The program code may execute on a single computer or on a plurality of computers. The computer may include a processing unit in communication with a computer-usable medium, wherein the computer-usable medium contains a set of instructions, and wherein the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. An apparatus for automatically mapping a verbatim narrative to a term in a medical terminology dictionary, comprising:
 a natural language processor configured to:
 process terms from the medical terminology dictionary and from a medical coding decision database to generate a processed database, the terms being processed by stemming, wherein the processed database also comprises the original terms from the medical terminology dictionary and the medical coding decision database; and
 process the verbatim narrative by stemming one or more words in the verbatim narrative;
 a comparator configured to compare the processed verbatim narrative as a whole to the terms in the processed database and determine whether the processed verbatim narrative as a whole is an exact match to a term in the processed database, wherein the verbatim narrative is mapped to the term in the medical terminology dictionary that corresponds to the term in the processed database that is an exact match; and
 a naïve Bayes classifier that, if there is no exact match, is configured to statistically analyze the verbatim narrative and map the verbatim narrative to the term in the medical terminology dictionary that is the closest match to the verbatim narrative, wherein the naïve Bayes classifier is a letters-based model if the probability of an assigned term is less than a pre-determined value and a words-based model if the probability exceeds the pre-determined value.

2. The apparatus of claim 1, wherein the medical terminology dictionary is a drug terminology dictionary and wherein the terms in the drug terminology dictionary comprise active ingredients of drugs.

3. The apparatus of claim 1, wherein processing the verbatim narrative comprises substituting for words in the verbatim narrative synonyms derived from the medical coding decision database or deleting words from the verbatim narrative that are considered inconsequential based on the medical coding decision database, or both substituting and deleting.

4. The apparatus of claim 3, wherein:
 before the natural language processor processes terms to generate the processed database, the comparator compares the verbatim narrative to the terms from the medical terminology dictionary, the term that is an exact match is selected, and the verbatim narrative is mapped to the term that is an exact match; and
 if there is no match, the comparator compares the verbatim narrative to terms from the medical coding decision database, the term that is an exact match is selected, and the verbatim narrative is mapped to the term in the medical terminology dictionary that corresponds to the term that is an exact match.

5. The apparatus of claim 4, wherein a second comparator performs at least one of the comparisons.

6. The apparatus of claim 1, wherein the natural language processor:
 cleans the verbatim narrative; and
 sorts the words in the verbatim narrative,
 wherein after each of these operations the comparator compares the processed verbatim narrative to the terms in the processed database and it is then determined whether the processed verbatim narrative is an exact match to a term in the processed database.

7. The apparatus of claim 1, wherein the medical coding decision database comprises auto-mappings to exact matches in the medical terminology dictionary.

8. The apparatus of claim 1, wherein the medical coding decision database comprises human-coded mappings to the medical terminology dictionary.

9. The apparatus of claim 1, wherein the medical coding decision database comprises auto-mappings to exact matches in the medical terminology dictionary and human-coded mappings to the medical terminology dictionary.

10. A method for automatically mapping a verbatim narrative to a term in a medical terminology dictionary, comprising:
 generating a processed database by processing through a natural language processor terms from the medical terminology dictionary and from a medical coding decision database, the term processing including stemming the terms, wherein the processed database also comprises the original terms from the medical terminology dictionary and the medical coding decision database;
 processing the verbatim narrative through the natural language processor by stemming one or more words in the verbatim narrative;
 comparing the processed verbatim narrative as a whole to the terms in the processed database;
 determining whether the processed verbatim narrative as a whole is an exact match to a term in the processed database;
 if there is a match, mapping the verbatim narrative to the term in the medical terminology dictionary that corresponds to the term in the processed database that is an exact match; and
 if there is no exact match,
  statistically analyzing the verbatim narrative using a naïve Bayes classifier that is a letters-based model if the probability of an assigned term is less than a pre-determined value and a words-based model if the probability exceeds the pre-determined value; and
  mapping the verbatim narrative to the term in the medical terminology dictionary that is the closest match to the verbatim narrative.

11. The method of claim 10, wherein the medical terminology dictionary is a drug terminology dictionary and wherein the terms in the drug terminology dictionary are active ingredients of drugs.

12. The method of claim 10, wherein processing the verbatim narrative through the natural language processor comprises substituting for words in the verbatim narrative synonyms derived from the medical coding decision database or deleting words from the verbatim narrative that are considered inconsequential based on the medical coding decision database, or both substituting and deleting.

13. The method of claim 10, further comprising:
 before generating the processed database, comparing the verbatim narrative to the terms from the medical terminology dictionary, selecting the term that is an exact match, and mapping the verbatim narrative to the term that is an exact match; and if there is no match, comparing the verbatim narrative to terms from the medical coding decision database, selecting the term that is an exact match, and then mapping the verbatim narrative to the term in the medical terminology dictionary that corresponds to the term that is an exact match.

14. The method of claim 10, wherein processing the verbatim narrative through the natural language processor further comprises:

cleaning the verbatim narrative; and sorting the words in the verbatim narrative, wherein after each of these operations:

the processed verbatim narrative is compared to the terms in the processed database; and the processed verbatim narrative is determined whether it is an exact match to a term in the processed database.

15. An apparatus for automatically mapping a concomitant medication (con-med) narrative to an active ingredient in a drug terminology dictionary, comprising:

a processed database comprising:

original active ingredients from the drug terminology dictionary;

original terms from a medical coding decision database that correspond to active ingredients in the drug terminology dictionary; and processed active ingredients from the drug terminology dictionary and processed terms from the medical coding decision database that correspond to active ingredients in the drug terminology dictionary;

a comparator configured to compare a processed con-med narrative to the active ingredients and terms in the processed database and to determine whether the processed con-med narrative is an exact match to an active ingredient or term in the processed database, wherein the con-med narrative is mapped to the active ingredient in the drug terminology dictionary that corresponds to the term in the processed database that is an exact match; and a naïve Bayes classifier that, if there is no exact match, is configured to statistically analyze the con-med narrative and map the con-med narrative to the active ingredient in the drug terminology dictionary that is the closest match to the con-med narrative, wherein the naïve Bayes classifier is a letters-based model if the probability of an assigned active ingredient is less than a predetermined value and a words-based model if the probability exceeds the pre- determined value.

16. The apparatus of claim 15, wherein the naïve Bayes classifier uses Laplace smoothing.

17. The apparatus of claim 15, wherein the naïve Bayes classifier is based on letter n-grams.

18. The apparatus of claim 17, wherein the naïve Bayes classifier uses 4-grams of letters.

19. The apparatus of claim 18, wherein the 4-gram letters-based model incorporates information from the drug terminology dictionary.

20. The apparatus of claim 15, wherein the naïve Bayes classifier is also based on word n-grams.

21. The apparatus of claim 20, wherein the word-based classifier incorporates information from the drug terminology dictionary.

22. The apparatus of claim 15, wherein the naïve Bayes classifier is also based on priors.

23. A method for automatically mapping a concomitant medication (con-med) narrative to an active ingredient in a drug terminology dictionary, comprising:

generating a processed database by processing through a natural language processor active ingredients from the drug terminology dictionary and terms from a medical coding decision database, wherein the processed database also comprises the original active ingredients from the drug terminology dictionary and the original terms from the medical coding decision database;

processing the con-med narrative through the natural language processor;

comparing the processed con-med narrative to the active ingredients and terms in the processed database;

determining whether the processed con-med narrative is an exact match to an active ingredient or term in the processed database;

if there is a match, mapping the con-med narrative to the active ingredient in the drug terminology dictionary that corresponds to the active ingredient or term in the processed database that is an exact match; and if there is no exact match, statistically analyzing the con-med narrative using a naïve Bayes classifier that is a letters-based model if the probability of an assigned term is less than a pre-determined value and a words-based model if the probability exceeds the pre-determined value; and mapping the con-med narrative to the active ingredient in the drug terminology dictionary that is the closest match to the con-med narrative.

24. The method of claim 23, wherein the naïve Bayes classifier is based on letter 4-grams.

* * * * *

UNITED STATES PATENT AND TRADEMARK OFFICE
CERTIFICATE OF CORRECTION

PATENT NO. : 11,023,679 B2
APPLICATION NO. : 15/443828
DATED : June 1, 2021
INVENTOR(S) : Allen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 330 days.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*